US011711429B2

(12) United States Patent
Henshaw et al.

(10) Patent No.: US 11,711,429 B2
(45) Date of Patent: Jul. 25, 2023

(54) METHOD FOR CALIBRATING NETWORKS OF ENVIRONMENTAL SENSORS

(71) Applicant: Aeroqual Ltd., Auckland (NZ)

(72) Inventors: Geoffrey Stephen Henshaw, Auckland (NZ); David Edward Williams, Kerikeri (NZ); Elaine Miles, Auckland (NZ); Georgia Miskell, Mount Maunganui (NZ); Lena Weissert, Auckland (NZ)

(73) Assignee: Aeroqual Ltd., Auckland (NZ)

( * ) Notice: Subject to any disclaimer, the term of this patent is extended or adjusted under 35 U.S.C. 154(b) by 0 days.

(21) Appl. No.: 16/776,733

(22) Filed: Jan. 30, 2020

(65) Prior Publication Data

US 2020/0244742 A1 Jul. 30, 2020

Related U.S. Application Data

(60) Provisional application No. 62/798,580, filed on Jan. 30, 2019.

(51) Int. Cl.
| | |
|---|---|
| *G06F 15/16* | (2006.01) |
| *H04L 67/125* | (2022.01) |
| *H04W 4/38* | (2018.01) |
| *G16Y 20/10* | (2020.01) |
| *G16Y 40/10* | (2020.01) |
| *G16Y 40/30* | (2020.01) |
| *G06F 17/18* | (2006.01) |
| *H04L 67/56* | (2022.01) |

(52) U.S. Cl.
CPC ............ *H04L 67/125* (2013.01); *G06F 17/18* (2013.01); *G16Y 20/10* (2020.01); *G16Y 40/10* (2020.01); *G16Y 40/30* (2020.01); *H04L 67/56* (2022.05); *H04W 4/38* (2018.02)

(58) Field of Classification Search
None
See application file for complete search history.

(56) References Cited

U.S. PATENT DOCUMENTS

| | | | |
|---|---|---|---|
| 7,539,593 | B2 | 5/2009 | Machacek |
| 9,291,608 | B2 | 3/2016 | Herzl |
| 10,281,167 | B2 | 5/2019 | Martin |
| 10,393,714 | B2 | 8/2019 | Wang |
| 10,605,633 | B2 | 3/2020 | Masson |

(Continued)

OTHER PUBLICATIONS

Miskell, G., Alberti, K., Feenstra, B., Henshaw, G., Papapostolou, V., Patel, H., Polidori, A., Salmond, J.A., Weissert, L. F., Williams, D.E., 2019. Reliable data from low-cost ozone sensors in a hierarchical network. Atmospheric Environment, 214, https://doi.org/10.1016/j.atmosenv.2019.116870.

(Continued)

*Primary Examiner* — Phyllis A Book
(74) *Attorney, Agent, or Firm* — Dentons US LLP

(57) ABSTRACT

Multiple low cost individual sensors communicate with a server. A proxy sensor communicates with the server. The server periodically compares information from the individual sensors with information from the proxy sensor. The server validates and accepts information from individual sensors. The server changes gain and offset values for individual sensors providing information that is not validated by the comparing.

15 Claims, 5 Drawing Sheets

(56) References Cited

U.S. PATENT DOCUMENTS

| | | | | |
|---|---|---|---|---|
| 2009/0076749 | A1* | 3/2009 | Nasle | G05B 17/02 718/1 |
| 2009/0325598 | A1* | 12/2009 | Guigne | G01S 5/021 455/456.1 |
| 2010/0030475 | A1* | 2/2010 | Sohl, III | G01N 1/4005 702/2 |
| 2012/0200457 | A1* | 8/2012 | Farrokhi | G01S 19/46 342/357.29 |
| 2014/0039823 | A1* | 2/2014 | Raghupathy | G01S 5/14 702/94 |
| 2014/0324351 | A1* | 10/2014 | Dannevik | G08B 21/10 702/3 |
| 2015/0248510 | A1* | 9/2015 | Meagher | G06Q 50/00 703/18 |
| 2016/0370334 | A1* | 12/2016 | van Tol | G01N 33/0008 |
| 2017/0023430 | A1* | 1/2017 | Dormody | G01C 5/06 |
| 2017/0208493 | A1* | 7/2017 | Masson | H04W 4/38 |
| 2017/0300602 | A1* | 10/2017 | Leeds | G01W 1/14 |
| 2018/0375680 | A1* | 12/2018 | Wright | F24D 19/1048 |
| 2019/0129409 | A1* | 5/2019 | Cella | G06N 20/00 |

OTHER PUBLICATIONS

Weissert, L.F., Alberti, K., Miskell, G., Pattinson, W., Salmond, J.A., Henshaw, G., Williams, D.E., 2019. Low-cost sensors and microscale land use regression: Data fusion to resolve air quality variations with high spatial and temporal resolution. Atmospheric Environment 213, 285-295.

Weissert, L.F., Alberti, K., Miles, E., Miskell, G., Feenstra, B., Henshaw, G.S., Papapostolou, V., Patel, H., Polidori, A., Salmond, J.A., Williams, D.E. 2020. Low-cost sensor networks and land-use regression: Interpolating nitrogen dioxide concentration at high temporal and spatial resolution in Southern California. Atmospheric Environment, 223, https://doi.org/10.1016/j.atmosenv.2020.117287.

\* cited by examiner

METHOD FOR CALIBRATING NETWORKS OF ENVIRONMENTAL SENSORS

Air quality regulatory monitors require frequent, rigorous calibration using standard reference materials in order to provide accurate and traceable environmental data. Such a calibration method is a significant operational cost and for that reason not economically feasible for low cost environmental sensor networks. A calibration method that reduces such costs is required in order to achieve useful data from high spatial density networks of low cost environmental sensors.

BACKGROUND OF THE INVENTION

One approach to sensor calibration is periodic co-location with a higher quality data source (reference) and to calculate calibration parameters such as slope and intercept using linear regression. However this approach has problems such as a) periods of missing data where the sensor has been removed for calibration, b) high costs due to intensive fieldwork requirements in regularly moving sensors for co-location, and c) inability to adapt to changes over time such as calibration drift. A modification of this approach is to make the reference mobile so that it visits each of the sensors in the network for a period of time to calibrate them. However this is not reliable since the pollutant levels must vary over a wide enough range during the time of the visit in order for the calibration to be reliable.

Another approach is to use a remote calibration technique based on cross-correlations between network locations often described as 'blind' calibration because this calibration method relies on no ground truth data to guide expectations. This method is not however robust against missing data and involves training a network using verified data to correct for extraneous influences. A practical limitation can be providing a sufficiently large training set of sufficiently good data.

Another approach is data fusion, which combines pollutant measurements with an atmospheric model. This approach is not traceable and assumes the stability of the sensor response which is not always the case.

Needs exist for improved calibrations of environmental sensors.

SUMMARY OF THE INVENTION

This invention provides a new approach that is economical to use, does not assume sensor stability, does not rely on training data and can update in real-time. The new calibration method adjusts the gain and offset of the sensor measurement to match the probability distribution of the sensor result to that of a proxy reference.

The invention includes adjusting gain and offset of the first sensor, so that over a selected period of time first probability distributions of adjusted first sensor measurements closely matches second probability distributions of the proxy reference. The proxy reference second probability distribution is a weighted combination of different data sources including a weighted combination of data from a regulatory air quality station, an air quality instrument with a traceable calibration, a collection of sensors, a satellite base instrument, a mobile air quality treatment and a computer model. The gain and offset values calculated from matching first probability distributions of first sensor and the proxy reference second probability distributions are stored and used locally on the first sensor and remotely on the server.

The server adjusts gain and offset of the first sensor, so that over a selected period of time first probability distributions of adjusted first sensor measurements closely matches second probability distribution of the proxy reference measurements. The proxy reference second probability distribution maybe a combination of different data sources, including a weighted combination of data from a regulatory air quality station, an air quality instrument with a traceable calibration, a collection of sensors, a satellite-based instrument, immobile air quality instrument and a computer model.

The gain and offset values calculated from matching the first probability distributions of the first sensor and the proxy reference second probability distributions are stored locally on the first sensor and remotely on the server.

If $X_i(t)$ denotes the true data value at location i and time t, then the sensor data, $Y_i(t)$, if the sensor response is linear over a range of expected measurements, will satisfy:

$$X_i(t) = a_0 + a_1 Y_i(t) \quad \{1\}$$

The new method then defines a reference data set from one or more regulatory or non-regulatory monitors located some distance from the sensor, which are a good estimate for the true concentration. It is assumed that the frequency distribution of measurements from a sensor and a suitable reference averaged over a time that captures the diurnal variations are similar. For air pollutants, such distributions are log-normal. Slope and offset estimates can then be derived by matching the mean and variance of the sensor to the reference distribution Z which is an estimate of the true distribution X.

Let $Z_i(t-t_d: t)$ denote the reference data and $Y_i(t-t_d:t)$ denote the sensor data for site i over the time interval $(t-t_d: t)$, then the slope, $\widehat{a_1}$ and offset, $\widehat{a_0}$, estimates for the corrected data are:

$$\widehat{a_1} = \sqrt{\frac{\mathrm{var}\langle Z(t-t_d:t)\rangle}{\mathrm{var}\langle Y(t-t_d:t)\rangle}} \quad \{1\}$$

$$\widehat{a_0} = E\langle Z(t-t_d:t)\rangle - \widehat{a_1} E\langle Y(t-t_d:t)\rangle \quad \{3\}$$

Where E< > denotes the arithmetic mean evaluated over the time period $(t-t_d:t)$ and var< > denotes the arithmetic variance about the mean. Then the estimate of $X_i$ at time t, $\hat{X}_{i,t}$:

$$\hat{X}_{i,t} = \hat{a}_0 + \hat{a}_1 Y_{i,t} \quad \{4\}$$

According to {2-4}, $E\langle \hat{X}(t-t_d:t)\rangle = E\langle Z(t-t_d:t)\rangle$ and $\mathrm{var}\langle(t-t_d:t)\rangle = \mathrm{var}\langle Z(t-t_d:t)\rangle$. Thus, if the distributions are characterized by only two parameters, then the site distribution over sample time $t_d$ is constrained to be the same as the reference distribution. More generally, the site distribution is constrained to be similar to the reference distribution for values around the mean. In practice this is not a limitation: the prior averaging time period, $t_d$, imposes an averaging filter on the data. It is empirically chosen to obtain a reasonable estimate of the distributions of Z and Y but is also chosen to average the short-term fluctuations and emphasize the longer-term, regular component of the concentration variation within the distribution of values. It is found that the frequency distribution of this longer term, regular component of variations of air pollutant concentration does indeed tend to be well correlated over extensive spatial regions, even though the variations might occur at different times of the day, or though local concentrations might show rather large excursions from the mean for relatively short times compared with the averaging time. If short-term fluctuations are particularly large, then data truncation can be used: the mean and variance of the test and reference distributions are simply matched over a data range that excludes the extreme fluctuations. The adjusted test data will then capture these fluctuations reliably.

The new approach can be combined with a rule-based framework that places constraints on the adjustment of the parameters $â_0$ and $â_1$. For example, the time series of $â_0$ and $â_1$ can be smoothed and the smoothed trend values used in equation 4. Other parameters can be used to determine whether the reference data set is reliable for particular conditions: for example particular wind directions might transport pollutants from other parts of the region being measured and bias the distributions with respect to one another. If such a condition occurred, it is a simple matter to implement a rule that uses the previous long-term trend value of the parameters $â_0$ and $â_1$, only updating when the reference condition returns to that where the distribution similarity is known to be valid.

If the sensor measurement comprises a linear combination of two parameters then the method would be modified thus.

$$C_{pollutant} = b_1 * C_{sensor1} + b_2 * C_{sensor2} + b_0$$

Where $C_{pollutant}$ is the pollutant measurement derived from sensor1 and sensor2 and $b_1$, $b_2$ and $b_0$ are parameters determined by the calibration method. The sensor is calibrated by matching the $C_{pollutant}$ measurements to that of a proxy ($P_{pollutant}$) and calculating the $b_1$, $b_2$ and $b_0$ values so that the Bayesian formulation defined below is satisfied.

$$\mathbb{P}(C_{pollutant}|C_{sensor1}, C_{sensor2}, \hat{b}_j) = \mathbb{P}(P_{pollutant})$$

The values of $b_1$, $b_2$ and $b_0$ are determined by using the mean (E(x)), standard deviation (SD(x)) and a third moment, (RT[x]) of $C_{pollutant}$ and $P_{pollutant}$, where RT[x] is defined below.

$$RX[x] = \sqrt[3]{\frac{\Sigma(x - E[x])^3}{n}}$$

Using initial values of $b_1 = b_2 = 1$; $b_0 = 0$, the parameters are optimised to minimise the objective function, $f(P_{pollutant}, C_{pollutant})$ defined as:

$$f(P_{pollutant}, C_{pollutant}) = (E[P_{pollutant}] - E[C_{pollutant}])^2 + (SD[P_{pollutant}] - SD[C_{pollutant}])^2 + (RT[P_{pollutant}] - RT[C_{pollutant}])^2$$

In principle, any number of sensors could be employed such that the result is a linear combination of the values given by each sensor. In that case, the number of moments of the distributions to be determined and matched using the objective function should equal the number of coefficients to be determined.

These and further and other objects and features of the invention are apparent in the disclosure, which includes the above and ongoing written specification, with the drawings.

DETAILED DESCRIPTION

Figure 1:
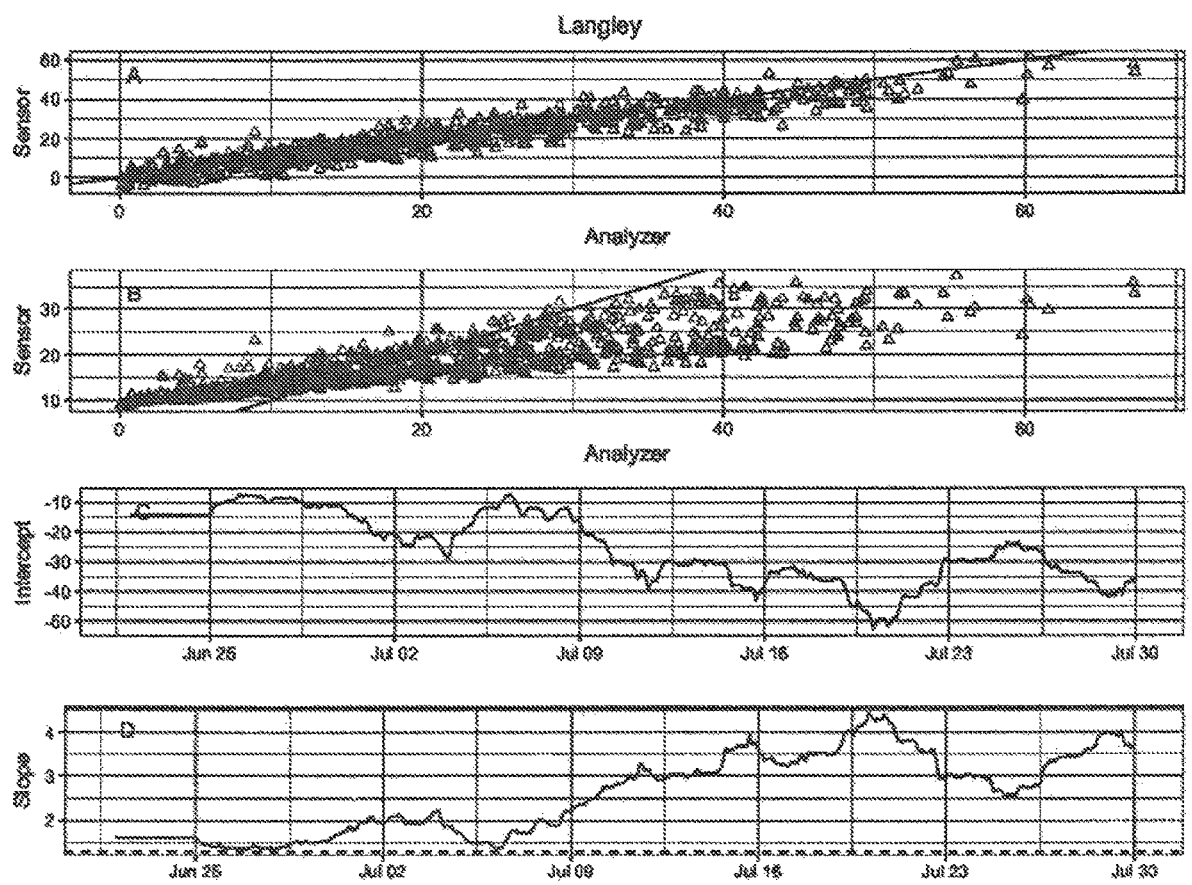
FIG. 1 shows the hourly-averaged raw data from the analyzers versus raw sensor data and calibrated sensor data using the new method.

We used a running averaging time $t_d = 72$ hours and examined a network of $O_3$ and $No_2$ sensors. FIG. 1 shows as an example the hourly-averaged raw data from the analyzers versus raw sensor data and calibrated sensor data using the new method. The method was successful in calibrating and routinely updating correct coefficient values for a poor sensor without any initial co-location requirement, despite the corrections being large.

FIG. 1 shows scatterplot of analyzer and semi-blind corrected sensor hourly-averaged data (earlier weeks=lighter triangles and later weeks=darker triangles). B is similar to A using raw sensor data. C is stepping $â_0$, and D is stepping $â_1$.

The method of deriving calibration coefficients by matching the mean and standard deviation of the data to that of a proxy has been shown to be a robust means of correcting data from drifting or mis-calibrated environmental sensors. The method is based on the idea that running over a time that is sufficiently long to remove the influence of short-term fluctuations but sufficiently short that results can be obtained in a practically useful time whilst still preserving the regular diurnal variations, the mean and standard deviation of measurements are highly correlated given an appropriate choice of reference. Reference choice made on the basis of distance or land-use similarity has been demonstrated to be effective. A running time of 72 hr is appropriate for diurnal air pollutants but this interval may be longer or shorter for different environmental measurements in different conditions. Sensor data corrected using this method measure reliably for data averaged over intervals from 1 minute. Use of data truncation in the proxy matching identified where the proxy and sensor data distributions differed and could be used to determine the reliability of the results.

Figure 2:
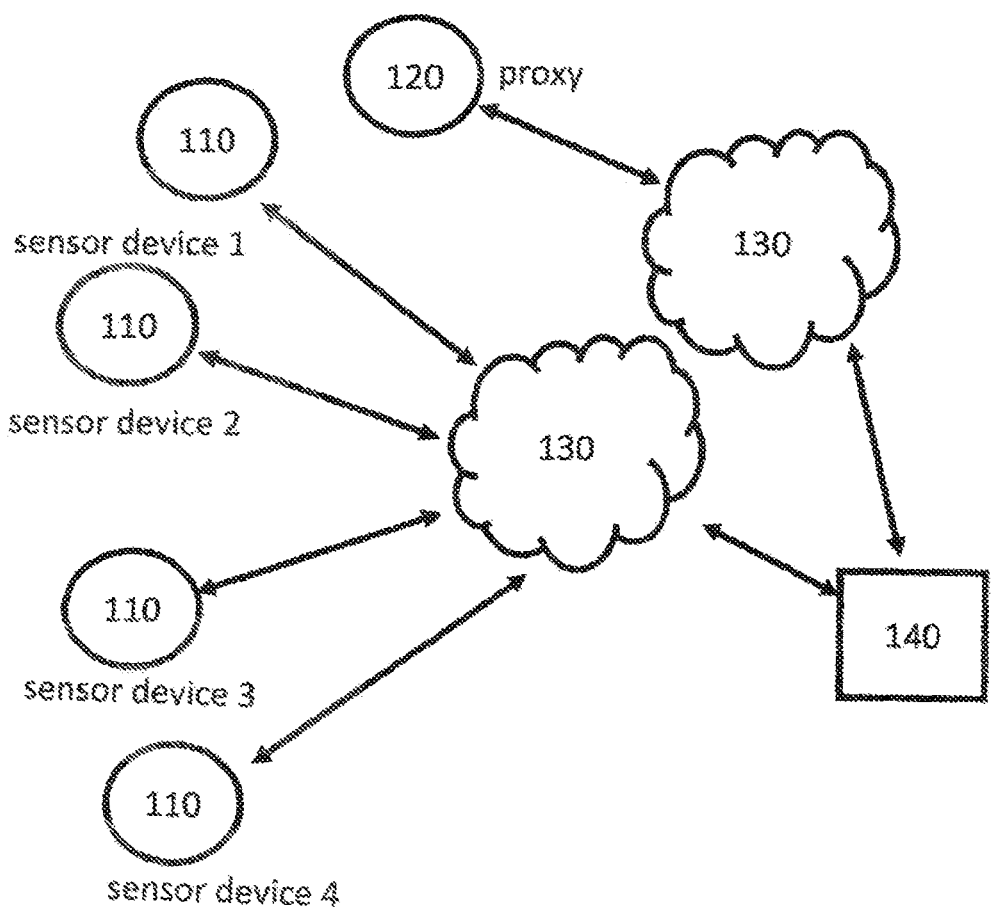
FIG. 2 is a diagram showing an example representation of a sensor network able to be calibrated by the new method.

FIG. 2 is a diagram showing an example representation of a sensor network able to be calibrated by the method. The sensor network can include a sensor device 110 and a proxy 120 in communication with a server device 140 over a network 130. The network 130 can include various types of networks, such as the Internet, a virtual private network (VPN), a wide area network (WAN), a local area network (LAN or VLAN), etc. The proxy 120 can include various types of reference instruments such as a regulatory air quality station, a calibrated gas instrument, a mobile instrument, a satellite or a computer model. The sensor devices 110 can transmit sensor data wirelessly to the server device 140 over the network 130. The proxy 120 can transmit proxy data wirelessly to the server device 140 over a network 130. The server device 140 can include a local storage device to store data associated with sensor data received from the sensor devices and proxy. The server device determines whether each sensor device 110 needs to be calibrated by comparing its data with data from the proxy 120. If it does, then the server device needs to be calibrated, calculates new gain and offset data using the method described. The sensor device can then send these gain and offsets back to the sensor device 110 over network 130 and adjust the sensor data stored on the server device 140.

Figure 3:
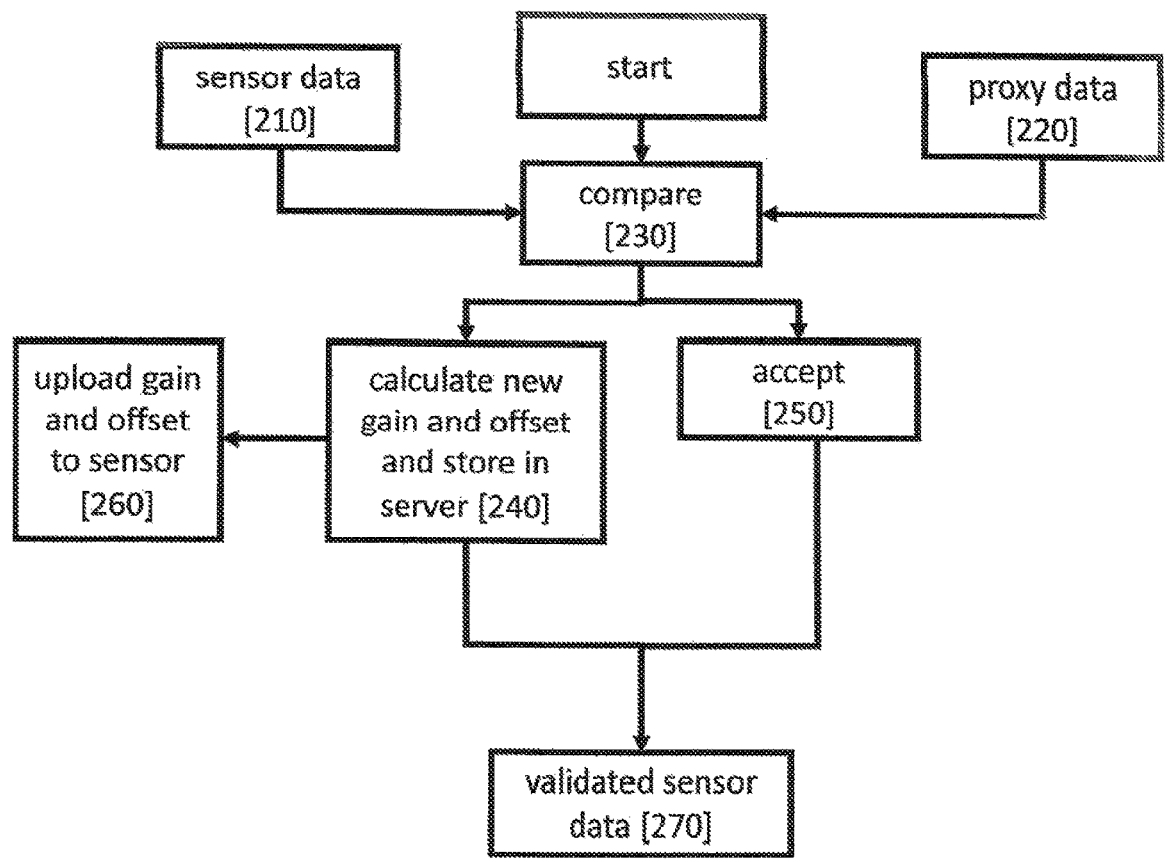
FIG. 3 is a process flow diagram showing how a sensor is calibrated.

FIG. 3 is a process flow diagram showing how a sensor is calibrated. The server 140 receives sensor data 210 and proxy data 220 and compares it 230 to see if the sensor data has drifted. If it has drifted server 140 calculates 240 new gain and offsets using the method described and stores them in the server. The gain and offset can be uploaded 260 to the sensor 110. If the sensor data has not drifted, the sensor data is accepted, and no new gain and offset is calculated or uploaded 250. The output of the process is validated sensor data 270 in the server 140.

Figure 4:
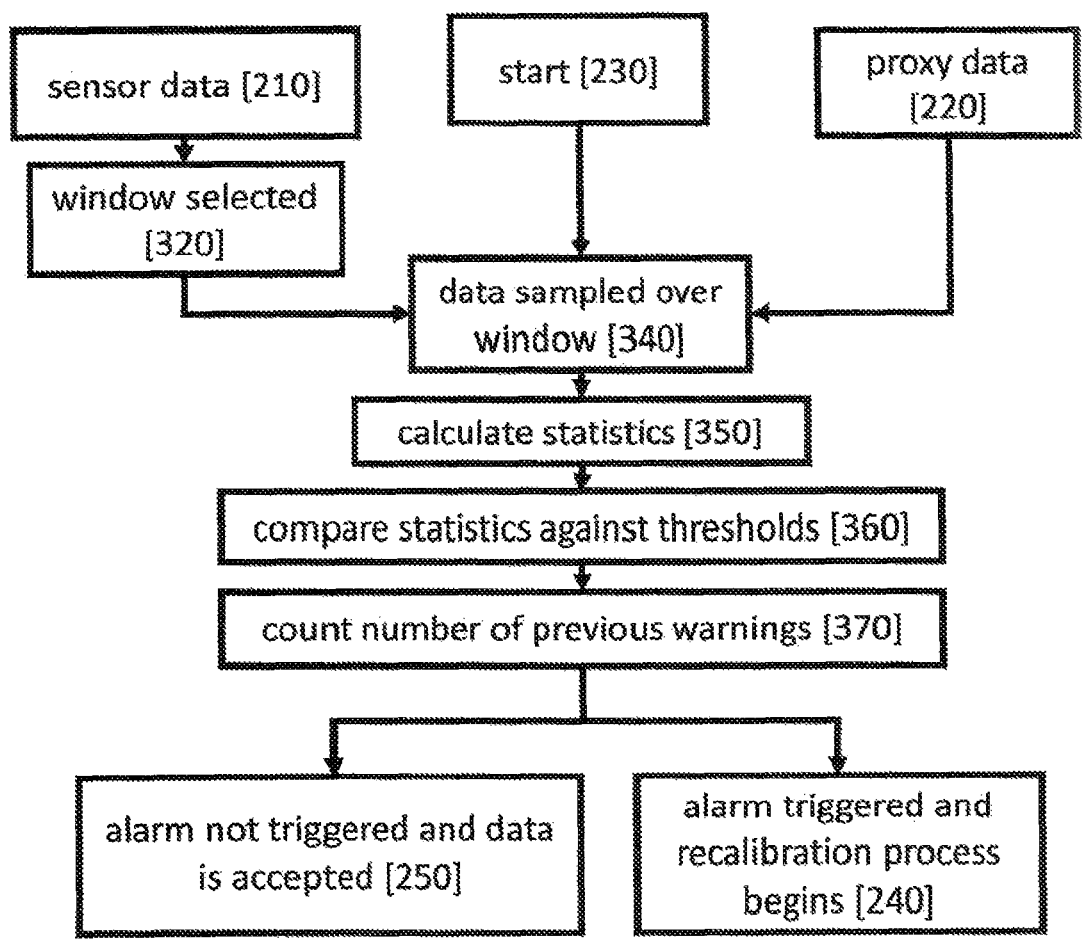
FIG. 4 is a process flow diagram showing how data is compared.

FIG. 4 is a process flow diagram showing how data is compared 230. Taking the sensor data 210, a window of time of a specified length and that includes at least one unvalidated sensor observation is selected 320. The sensor data and proxy data 220 are sampled over the window 340. Comparative statistics between the sampled sensor and proxy data are calculated 350. The statistics are compared against threshold values, setting off warnings if they are exceeded 360. The number of consecutive warnings is counted 370, and if it equals a specified threshold, an alarm is triggered. If the alarm is triggered, the system enters the recalibration process 240. If the alarm is not triggered, the process ends 250.

Figure 5:
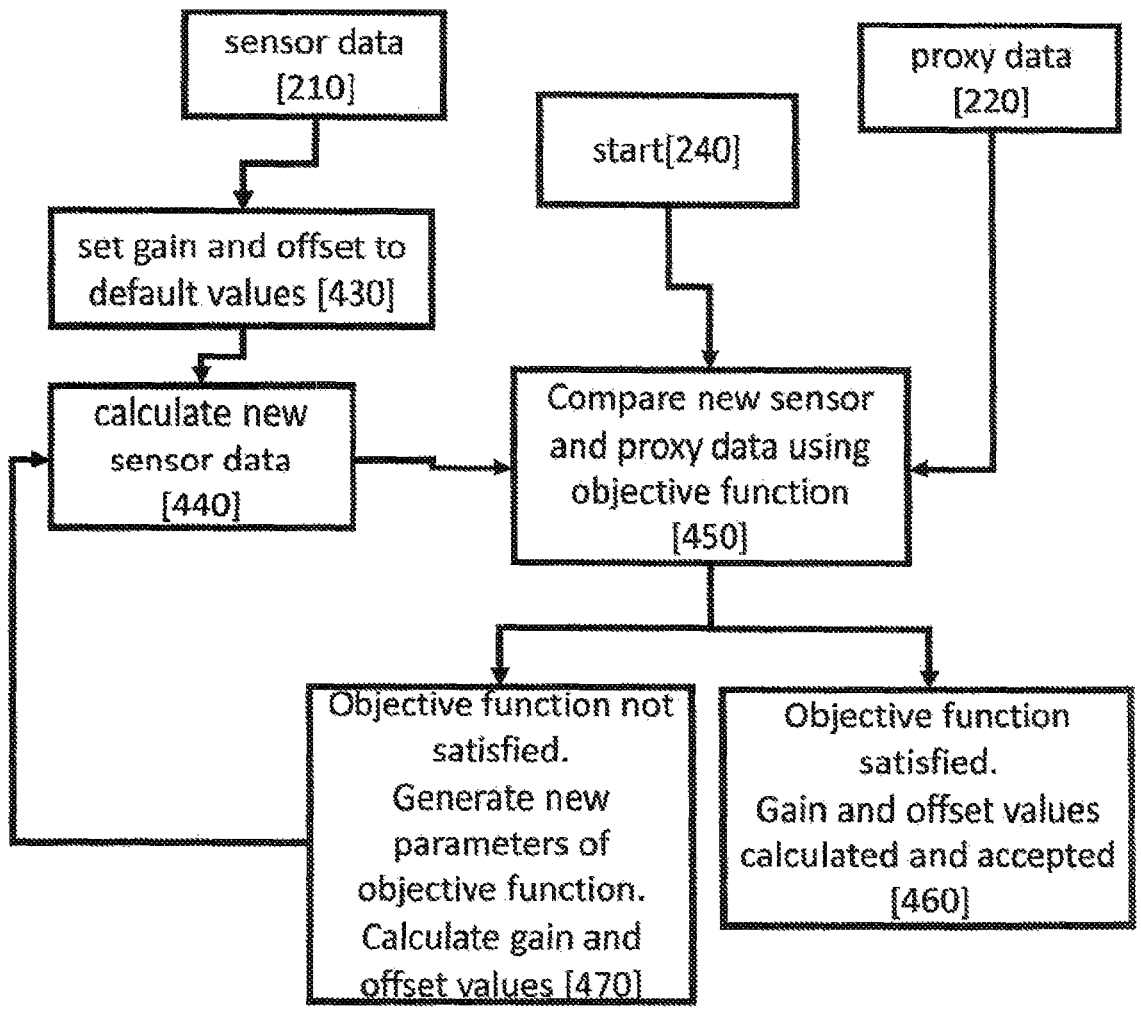
FIG. 5 is a process flow diagram showing how gain and offset values for a sensor are calculated.

FIG. 5 is a process flow diagram showing how gain and offset values for a sensor are calculated 240. A sample of uncalibrated sensor data 210 and proxy data 220 is collected. The gain and offset values are set to default values 430 and are applied to generate new sensor data 440. The new sensor data is assessed against the proxy data using an objective function 450. If the objective function is satisfied the offset and gain values are accepted 460 and the process ends. If the objective function is not satisfied, then new input parameters are generated for the objective function which generates new gain and offset values 470. New sensor data is calculated and comparison process is repeated 440.

While the invention has been described with reference to specific embodiments, modifications and variations of the invention may be constructed without departing from the scope of the invention.

The invention claimed is:

1. A computer implemented method for performing calibration in a network of environmental sensors comprising a plurality of spatially distributed sensor devices and a proxy, each of the plurality of spatially distributed sensor devices configured to measure an air pollutant concentration, and each of the plurality of spatially distributed sensor devices and the proxy in communication with a central server over a data network, the method comprising:
  receiving, at the central server:
    sensor data associated with each of the plurality of spatially distributed sensor devices, and
    proxy data associated with the proxy, the proxy data representing an estimate for an air pollutant concentration at the site;
  determining, at the central server:
    a drift in the sensor data for each spatially distributed sensor device, the determination of the drift in the sensor data being calculated by comparing the received sensor data from each sensor device amongst the plurality of spatially distributed sensor devices to the received proxy data;
    a probability distribution for the sensor data and a probability distribution for the proxy data to calculate a gain and an offset for the drifted sensor data over a selected period of time;
  performing, at the central server, a sensor calibration operation by adjusting the calculated gain and offset of each spatially distributed sensor device, such that over the selected period of time, the probability distribution of the drifted sensor data substantially matches the probability distribution of the proxy data; and
  storing, in a database on the central server, the calibrated sensor data indicating an air pollutant concentration at the site.

2. The method of claim 1, wherein the selected period of time in which the probability distributions of the drifted sensor data and the proxy data are matched is time taken to capture diurnal variations of the measured air pollutant.

3. The method of claim 1, wherein the plurality of spatially distributed sensor devices are each configured to measure any one or more of air pollutants including ozone, nitrogen dioxide, sulphur dioxide, carbon monoxide, hydrogen sulphide, ammonia, carbon dioxide, or methane.

4. The method of claim 1, wherein the proxy comprises any one or more of a regulatory air quality station, an air quality instrument with a traceable calibration, a collection of sensors, a satellite-based instrument, a mobile air quality instrument, or a computer model.

5. The method of claim 1, wherein the probability distribution of the proxy is computed from a combination of different data sources, including but not limited to data from a regulatory air quality station, an air quality instrument with a traceable calibration, a collection of sensors, a satellite-based instrument, a mobile air quality instrument, and a computer model.

6. The method of claim 1, wherein the proxy is selected on the basis of similarity in land use to the site where the sensor is placed.

7. The method of claim 1, wherein the gain and offset values calculated from matching probability distributions of the drifted sensor data and the proxy data are stored locally on each spatially distributed sensor device.

8. The method of claim 1, wherein the method further comprises:
  computing trend values of gain and offset for the drifted sensor data.

9. The method of claim 1, wherein the method further comprises:
  determining whether the calculated gain and offset of the drifted sensor data should be corrected based on direction of wind.

10. A sensor network apparatus for determining an air pollutant concentration at a site, the apparatus comprising:
  a plurality of spatially distributed sensor devices and a proxy, each of the plurality of sensor devices configured to measure air pollutant concentration, and each of the plurality of spatially distributed sensor devices and the proxy in communication with a central server over a data network;
  a processor and a computer program product, the computer program product comprising a non-transitory computer useable medium including a computer readable code,
  wherein the computer readable code when executed using one or more computing device processors, causes the one or more computing processors to operate the sensor network to:
  receive, at the central server:
    sensor data from each of the plurality of spatially distributed sensor devices, and
    proxy data associated with the proxy, the proxy data representing an estimate for an air pollutant concentration at the site;
  determine, at the central server:

a drift in sensor data, the determination of the drift in the sensor data being calculated by comparing the received sensor data from an individual sensor device amongst the plurality of spatially distributed sensor devices to the received proxy data; and separately validate, at the central server, the received sensor data to any future sensor data to be received from each of the plurality of spatially distributed sensors.

11. The apparatus of claim 10, wherein the central server is configured to calculate gain and offset for each of the plurality of spatially distributed sensor devices based on a probability distribution for the sensor data and a probability distribution for the proxy data, and wherein the central server is configured to upload the calculated gain and offset into each of the plurality of spatially distributed sensors.

12. The apparatus of claim 10, wherein the central server is adapted to select windows of data to be received from each individual sensor and to compare the data received during each window, and wherein the central server is further adapted to calculate statistics to compare against a threshold and to count a number of process warnings, to accept data if the threshold is met, and to trigger a recalibration process for any individual sensor from which data is received when the threshold is not met.

13. The apparatus of claim 10, wherein the central server is further configured to:
   i. set gain and offset values for each of the plurality of spatially distributed sensor devices to default values;
   ii. receive data comprising the default values from each of the plurality of spatially distributed sensor devices, and compare the received data from each of the plurality of spatially distributed sensor devices with data from the proxy using an objective function;
   iii. generate new parameters for the gain and the offset for each of the plurality of spatially distributed sensors,
   iv. recalculate the gain and offset for each of the plurality of spatially distributed sensors, and compare the data from each individual sensor with the data from the proxy,
   v. accept an individual sensor amongst the plurality of spatially distributed sensors, if the objective function for that sensor is satisfied, and if the objective function for that sensor is not satisfied, then repeat steps (iii)-(iv) for that individual sensor.

14. The apparatus of claim 13, wherein the central server is adapted to repeat the compare of step (ii) for the new data with the new gain and offset for said individual sensor.

15. A sensor network apparatus for determining an air pollutant concentration at a site, the apparatus comprising:

a plurality of spatially distributed sensor devices and a proxy, each of the plurality of sensor devices configured to measure air pollutant concentration, and each of the plurality of spatially distributed sensor devices and the proxy in communication with a central server over a data network;

a processor and a computer program product, the computer program product comprising a non-transitory computer useable medium including a computer readable code, wherein the computer readable code when executed using one or more computing device processors, causes the one or more computing processors to operate the sensor network to:

receive at the central server:
   sensor data from each of the plurality of spatially distributed sensor devices, and
   proxy data associated with the proxy, the proxy data representing an estimate for an air pollutant concentration at the site;

determine, at the central server:
   a drift in sensor data, the determination of the drift in the sensor data being calculated by comparing the received sensor data from an individual sensor device amongst the plurality of spatially distributed sensor devices to the received proxy data; and separately validate, at the central server, the received sensor data to any future sensor data to be received from each of the plurality of spatially distributed sensors, and wherein the central server is further configured to:
   i. set gain and offset values for each of the plurality of spatially distributed sensor devices to default values;
   ii. receive data comprising the default values from each of the plurality of spatially distributed sensor devices, and compare the received data from each of the plurality of spatially distributed sensor devices with the proxy data using an objective function;
   iii. generate new parameters for the gain and the offset for each of the plurality of spatially distributed sensors,
   iv. recalculate the gain and offset for each of the plurality of spatially distributed sensors, and compare the data from each individual sensor with the data from the proxy,
   v. accept an individual sensor amongst the plurality of spatially distributed sensors, if the objective function for that sensor is satisfied, and if the objective function for that sensor is not satisfied, then repeat steps (iii)-(iv) for that individual sensor.

* * * * *